United States Patent [19]

Guillet et al.

[11] Patent Number: 5,482,719
[45] Date of Patent: Jan. 9, 1996

[54] DRUG DELIVERY SYSTEMS

[76] Inventors: James E. Guillet, 31 Sagebrush Lane, Don Mills, Ontario, Canada, M3A 1X4; Hamid Bakhtiyari, 29 Rowe Court, Markham, Ontario, Canada, L3S 2J6

[21] Appl. No.: 971,996

[22] Filed: Oct. 30, 1992

[51] Int. Cl.$^6$ ..................................................... A61K 9/14
[52] U.S. Cl. ..................... 424/486; 424/485; 424/78.38; 424/78.31; 424/78.37; 424/451
[58] Field of Search .................................... 424/486, 485, 424/78.38, 451, 78.08, 78.37, 78.31

[56] References Cited

U.S. PATENT DOCUMENTS

| 4,766,037 | 9/1988 | Watanabe et al. | 428/402.21 |
| 5,258,453 | 11/1993 | Kopecek et al. | 525/54.1 |

FOREIGN PATENT DOCUMENTS

91/05816  5/1991  WIPO.

OTHER PUBLICATIONS

Mamada et al., "Photoinduced Phase Transition of Gels", Macromolecules 1990, 23, 1517–1519.
Kwon, et al., "Nature" (1991), 354,291–293.
Peterson et al., "Controlled Release of Bioactive Materials"; Ed. by Richard Baker, RS/201/D415/1979 pp. 45–53.
Collect. Czech Chem. Commun., 1987, vol. 52, pp. 1352–1355, Younes, M. E. et al. "Synthesis of Elastin–Like Peptides Using the Liquid Phase Method".
Chemical Abstracts, vol. 107, No. 23, 7 Dec. 1987, Columbus Ohio, US; abstract No. 214271, Yen, Hung Ren et al., "Synthetic Water–Soluble Copolymers for Optically–Controlled Ligand Delivery" see abstract & Poly. Mater. Sci. Eng. 1987, vol. 57 pp. 243–247.
Journal of the American Chemical Society, vol. 97, No. 6, 19 Mar. 1975, Washington, D.C., U.S.A., pp. 1575–1579 D. H. Rich & S. K. Gurwara "Preparation of a New O–Notribenzyl Resin for Solid–Phase Synthesis . . . " Cited in the appln. see whole doc.
Bioconjugate Chem., vol. 3, No. 2, pp. 104–107, Mar./Apr. 1992, Goldmacher V S et al "Photoactivation of Toxin Conjugate" see whole document.
Biological Abstracts, vol. 81, Philadelphia, Pa. US; Abstract No. 015704 Senter P D et al. "Novel Photocleavage Protein Crosslinking . . . " see abstract & Photochemistry and Photobiology, vol. 42, No. 3 pp. 232–238, 1984.
Chemical Abstracts, vol. 110, No. 11, 13 Mar. 1989, Columbus, Ohio, US; abstract No. 095775, Yoneis, M. E. et al. 'An Improved Application of the Photosensitive . . . ' see abstract & J. Indian Chem. Soc., 1988 vol. 65, pp. 498–499.
Chemical Abstracts, vol. 110, No. 22, 29 May 1989, Columbus, Ohio, US; abstract No. 193552, Yen, Hung Ren et al. "Optically Controlled Ligand Delivery . . . " see abstract & Makromol. Chem. 1989, vol. 190, pp. 69–82.
Biochem Int. Apr. 1992, vol. 26, No. 5, pp. 943–951, Marriott G et al. "Photomodulation of the Nucleating Activity of a Photocleavable Crosslinked Acting Dimer" see Abstract.
Proc Natl Acad Sci USA, Dec. 1980, vol. 77, No. 12, pp. 7237–7241, McCray J. A. et al. "A New Approach to Time–Resolved Studies of ATP–Requiring Biological Systems . . . " see p. 7237, see p. 7240.
Chem. Lett., 1989, No. 3, pp. 433–436, Kusumi, Akihiro et al "Liposomes That Can Be Disintegrated By Photo–Irradiation".
Bioconjugate Chem. 1990, vol. 1, No. 4, pp. 296–304. Koch Troels et al. "The Oxidative Cleavability of Protein Cross–Linking Reagents Containing Organoselenium Bridges" pp. 297–298.
Pharmazie, vol. 32, No. 11, Nov. 1977, Berlin DD, Pawelczyk E. et al. "Kinetics of Drug Decomposition Part 51: Kinetics of Indometacine Photodegradation".

*Primary Examiner*—Thurman K. Page
*Assistant Examiner*—William E. Benston, Jr.

[57] ABSTRACT

A photoactivatable drug delivery system is provided, in which a drug is combined e.g. by covalent bonding, incorporation in a matrix or encapsulation, with a photosensitive macromolecule. In combination, the drug is inert. The macromolecule is large enough to prevent migration of the combination within the body, so that the combination can be implanted at a location of maximum effectiveness. The drug is released from the combination, in therapeutically active form, upon appropriate irradiation.

24 Claims, 1 Drawing Sheet

IRRADIATION OF NA-NBA-Et

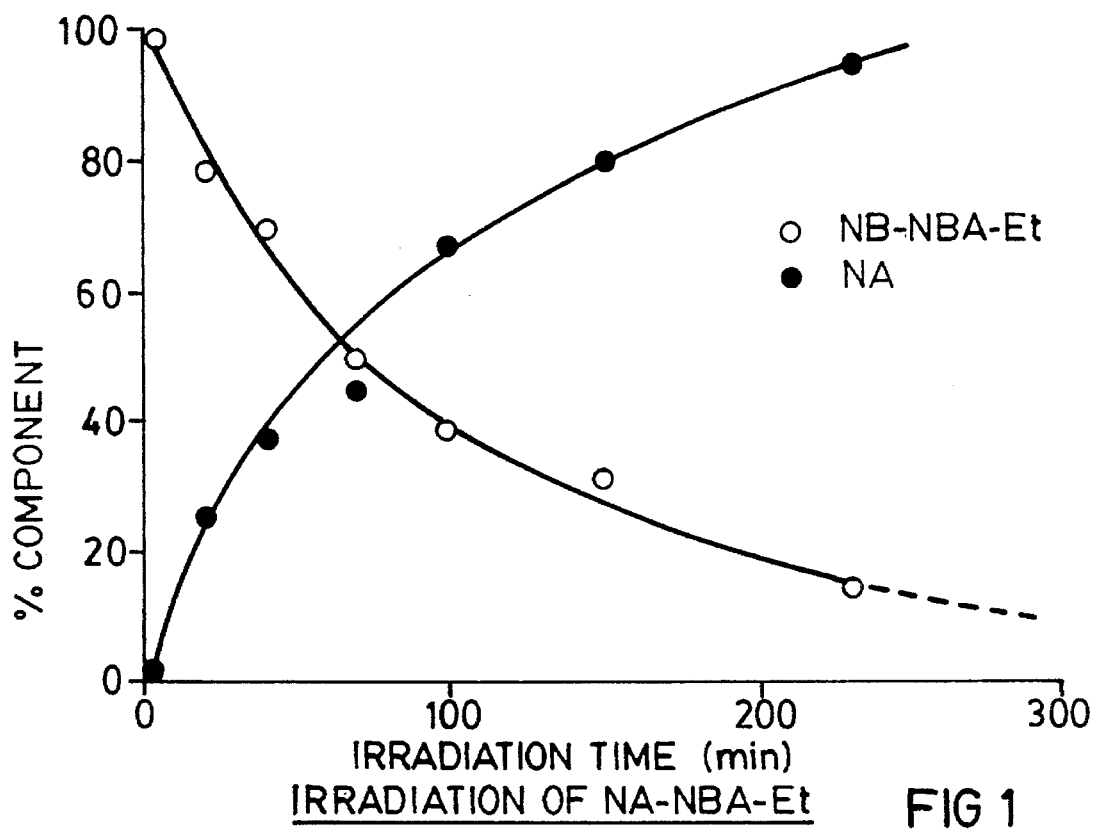
IRRADIATION OF NA-NBA-Et  FIG 1
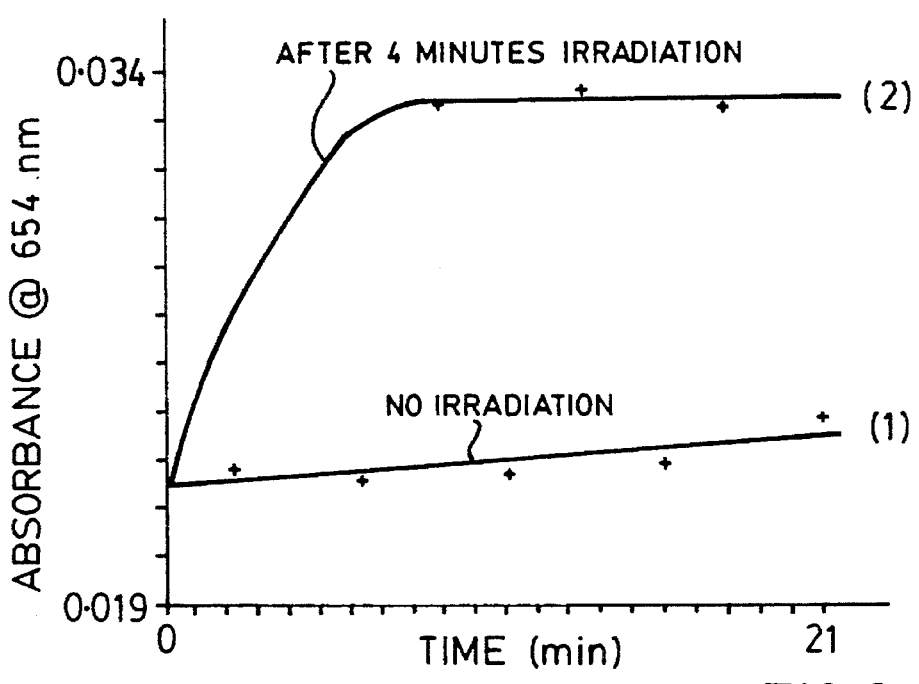
FIG. 2

DRUG DELIVERY SYSTEMS

FIELD OF THE INVENTION

This invention relates to drug delivery systems, and more particularly to systems whereby a drug can be delivered to the organ or body part of a patient where its effect is required, and released for activity at such locations in controlled amounts.

BACKGROUND OF THE INVENTION

The usual methods of drug administration are the oral ingestion of tablets, capsules, liquid drug formulations etc., parenteral administration into the blood stream or tissues, and rectal suppository administration. Such methods are far from ideal, since they provide wide variations in plasma concentration of drugs at different times between dosages, ranging from ineffectively low concentrations to toxic levels at which harmful side effects can be experienced. Moreover, such methods are essentially non-site specific, and deliver the drug to substantially all parts of the body and all body organs, not just the area needing treatment by the drug. Accordingly, such methods are wasteful in terms of amounts of drugs used, and also possibly harmful in subjecting body parts and organs to foreign substances having no need for treatment by them.

A particular form of drug therapy where localized action of the drug is important is cancer therapy. Drugs which are effective in attacking malignant cells to limit their proliferation have a tendency to attack benign cells also, so that it is highly desirable to limit the location of their action to that of the malignancy, and to ensure that effective but not excessive amounts of such drugs are used, at any particular time. Previous attempts to administer such drugs by direct injection into the location or organ having the malignancy are only partially effective, because of leakage of the drug from this location. Such leakage cannot be totally prevented, with the result that excessive quantities need to be administered.

It is an object of the present invention to provide novel drug delivery systems.

It is a further object to provide novel compositions of pharmaceuticals which can be delivered to specific treatment sites in a body, and released thereto in a controlled manner.

SUMMARY OF THE INVENTION

The present invention provides biologically acceptable combinations of drugs with polymeric materials, the drug being inactive whilst in the combination but active when released therefrom. The combination of drug and polymer is so large, on a molecular scale, that the drug is effectively prevented from diffusing or otherwise separating therefrom, under normal circumstances, and the combination can be effectively localized at a body location. The association between the drug and polymer is one of chemical bonding, physical dispersion and complexing, or encapsulation, but in any event is one which can be broken at will by photoactivation, to release from the combination active drug for therapeutic action when the composition is at the required location in the body, in controlled amounts and in the appropriate dosage rates over time. The release of the drug from the polymer combination is accomplished by appropriate radiation directed at the location of the polymer-drug combination from outside the body, by an operator, in a controlled manner. In this way, slow release of appropriate dosage levels can be arranged, rather than short bursts of excessive initial quantities.

In a first general embodiment of the invention, the drug is chemically covalently bonded to the polymer through the intermediary of a photolabile chemical bond. Upon being subjected to radiation of appropriate wavelength, the covalent bond is broken to release the drug. The number of such bonds broken, and hence the amount of drug released, is determined by the radiation dosage. The drug thus covalently linked to the polymer may be used as such, or used in admixture with a hydrogel or similar polymer complex.

In a second general embodiment of the invention, the drug is physically dispersed in an insoluble polymeric complex of biologically acceptable polymer or polymers, the complex being capable of swelling in water. The complex undergoes a dimensional change on being subjected to appropriate radiation, thereby releasing the drug for therapeutic action in a controlled manner in which released amounts are dependent upon the dosage of radiation supplied. Similarly, when radiation is discontinued, the complex will regain its original dimensions, thereby allowing for pulsed delivery of the therapeutic agent over time.

In a third general embodiment, the drug is encapsulated or embedded in films of photodegradable, biologically acceptable polymers, and delivered to the required body site in such a form. The drug is released, at a controlled rate, by irradiation to degrade the polymeric film and render it permeable to the drug to a controlled extent for controlled release.

In a fourth general embodiment, the drug is combined physically or chemically, or by a combination of physical and chemical means, in a liquid solution or emulsion with the polymer, and applied topically to the area of treatment. Again the drug is inactive in combination with a polymer, but is released therefrom in active form upon appropriate irradiation of the combination.

In respect of the first three general embodiments, where the combination is internally administered, the delivery of the polymer-drug combination to the desired body site can be arranged in one of a number of different ways. The combination can be chosen, in respect of polymer choice, to arrange that the combination will pass certain but not all body membranes, thereby arranging for its migration to the appropriate body location. Alternatively, and preferably, the combination can be administered by direct injection or implantation to the appropriate body location. Since the radiation to release the drug in active form is directed specifically at the location where treatment is required, active drug is only released there and not elsewhere in the body. Thus minor amounts of the polymer-drug combination which is itself effectively inert from a biochemical viewpoint elsewhere in the body, is not a serious problem.

Radiation for release of the drug in its active form from the drug-polymer combination can be by one of a variety of means, depending upon the photo sensitivities of the chosen photolabile bond, the polymer and the drug. It can be use of electromagnetic radiation, for example infrared, visible or ultraviolet radiation, supplied from incandescent sources, natural sources, lasers including solid state lasers or even sunlight. Administration thereof can be by external radiation or internal radiation, e.g. by use of fibre optic light pipes. After introduction of the compounds of the present invention to the patient at the required body sites, the patient can in many instances self-administer the radiation to release drug on an "as required" basis, e.g. for hypertension treatment or for pain relief.

BRIEF REFERENCE TO THE DRAWINGS

FIG. 1 is a graphical presentation of the results obtained according to Example 6 below.

FIG. 2 is a graphical presentation of the results obtained according to Example 15 below.

DESCRIPTION OF THE PREFERRED EMBODIMENTS

One preferred embodiment of the present invention is a chemical complex of a biologically acceptable polymer and a therapeutic compound, chemically bonded together through a photolabile covalent chemical linkage. Since body tissues tend to absorb radiation in the ultraviolet region of the electromagnetic spectrum, it is preferred to choose a photolabile bond sensitive to red and infrared wavelengths. Alternatively, a fibre optic light pipe, injected into the body to the vicinity of the treatment area, and protruding to the outside of the body in the manner of a cannula, can be adopted so that any appropriate wavelength of radiation can be chosen. This can if desired be left semi-permanently in place, for periodic use to supply appropriate dosage release at appropriate intervals. The amount of drug released is proportional to the dosage of the radiation. Such fibre optic light pipes are known and used in various types of medical treatments, for example irradiation treatment of internal body organs such as bladder irradiation.

The photolabile group should be one which, on radiation, releases the drug from the polymer in its therapeutically active form. It should not be one which releases the drug as a chemical complex bound to the polymer fragments or linked to intermediate linking compound fragments, in case these fragments have a deactivating effect on the biochemical potency of the drug. Thus the polymer itself should not contain chemical bonds which are photo-sensitive to the radiation to be used to release the drug. The only photosensitive groups in the linking compounds should be those linking them to the drug, and these should be arranged and located so that, with the chosen radiation, the drug is released in therapeutically active form.

The drug may be released from the polymer combination by direct radiation, or through the intermediary of a photosensitizer. In this latter method, a biologically acceptable photosensitive compound is included in the combination, the compound being capable of absorbing radiation to raise it to an excited state, and transferring its absorbed energy to the polymer-drug combination to effect the release of the drug therefrom, in an active form. The use of photosensitizers in this way is particularly suitable where the drug or the polymer has other chemical bonds sensitive to the same wavelength of radiation as the aforementioned photolabile group, so that direct radiation might deactivate the drug or decompose the polymer. Sensitizers allow a different wavelength of radiation to be used.

Useful linking compounds for the present invention can be found among those compounds known as photolabile peptide blockers. These are used in peptide chemistry, to react with and chemically block the carboxylic acid terminal group or the amine terminal group of a peptide whilst other chemical manipulations are conducted. Subsequently, they are photochemically removed, to restore the free acid or amine group. There is extensive literature on photolabile peptide blockers, from which the skilled worker can select appropriate compounds, in conjunction with chosen polymers and drugs, for use in the present invention.

One specific example of such a linking compound providing a photolabile group for use in the present invention is 4-bromomethyl-3-nitro-benzoic acid (BNBA), which has the chemical formula:

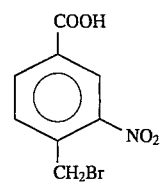

In this compound, the bromomethyl group is available for covalent coupling to a functional group, more specifically a nucleophilic functional group on a drug molecule. The carboxylic acid group is available for covalent bonding to functional groups on a food grade polymer. BNBA is a known compound, used as a photochemically removable blocking group in protein synthesis. Another useful, and similar compound, is 4-hydroxymethyl-3-nitrobenzoic acid, HNBA.

Another useful such linking compound providing a photolabile bond is [4-(2-chloropropionyl)phenyl]acetic acid, CPA, which has the formula:

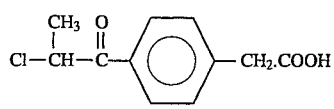

The chlorine group of CPA is available for reaction with a nucleophilic functional group of the drug molecule, and the carboxylic acid group is available for covalent attachment to a polymer, e.g. through an ester or amide linkage. Analogous compounds, i.e. those corresponding to the general formula:

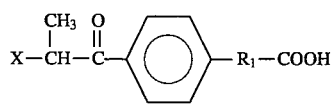

where X is halogen, R is H or lower alkyl C1–C4 and R1 is lower alkylene C1–C4, can also be used. The photolability resides in the keto carbonyl group associated with the adjacent CHR grouping.

Another specific example of a photolabile group for use in the present invention is a carbamate group linked to certain substituted aromatic rings, and in which the —NH— group thereof is derived from an amino group of the drug, e.g.

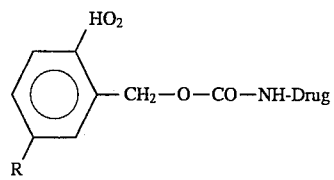

where R is H or lower alkoxy, and

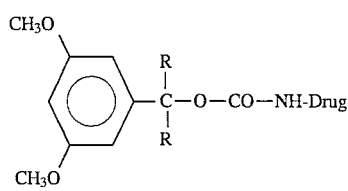

where R is H or lower alkyl.

These can be formed by reacting the appropriate oxycarbonyl chloride compound with a primary amine group on the drug molecule. Upon appropriate radiation, carbon dioxide is eliminated and the drug-$NH_2$ grouping is restored.

In preparing the covalent chemical complex of this aspect of the present invention, it is preferred to link the photolabile compound to the polymer first, and to link the drug to the photolabile groups thereon subsequently. A wide choice of polymers are available for this purpose. The polymer should of course be biochemically acceptable and inert, and is preferably an approved food grade polymer. It needs to possess chemical groups capable of reaction with a functional group of the photolabile compound such as the carboxylic acid group of BNBA or CPA, e.g. hydroxyl groups. The polymer should also be either indigestible or only slowly digestible by the body, so that it remains substantially intact whilst the controlled release of the drug therefrom is undertaken. The molecular weight of the polymer can thus vary widely, depending to some extent on the method of administration and the body locality to be treated. It can be as low as 250 in some circumstances, and high as one million. The polymer should be a large enough macromolecule that it will remain substantially localized at the body site during treatment, and not be reabsorbed into the circulatory system of the body prematurely. It should also be capable of releasing the active drug freely, once the covalent chemical bonding has been broken, i.e. the drug must be able to diffuse out of the residual polymer matrix in the presence of body fluids. Examples of suitable polymers include edible polysaccharides such as starch and starch derivatives, e.g. hydroxyethyl starch, cyclodextrin, polyvinyl alcohol (PVA), polyethylene oxide (polyethylene glycol PEG), acrylamide copolymers, vinylpyrrolidone copolymers, hydroxyl functionalized polylactides, poly (hydroxyethyl methacrylate) (HEMA), copolymers of two or more such monomers, e.g. copolymers of vinylpyrrolidone and HEMA, and copolymers of ethylene oxide and propylene oxide.

When the polymer has chlorine or bromine groups attached thereto, and the drug contains a carboxyl group, the drug can be linked to the polymer by means of an ester group, following derivatization of the polymer to provide a suitable labile linkage, e.g. using BNBA, CPA or HNBA. Thus the polymer may initially be reacted with BNBA thus:

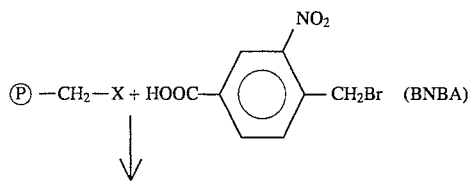

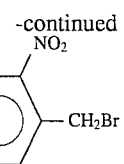

Then reaction with the carboxyl group of the drug moiety is conducted, to give a compound which can be generally represented

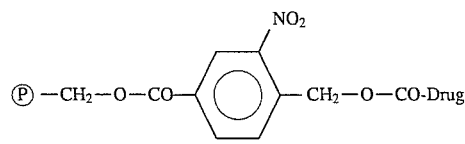

These two reactions can if desired be conducted in the reverse order. Appropriate radiation reforms the active drug-COOH.

When the polymer similarly has chlorine or bromine groups attached thereto, and the drug contains a hydroxyl group, the drug can similarly be linked to the polymer group through the intermediary of a photolabile group such as a residue of BNBA, CPA or HNBA, e.g. to give a photolabile compound of formula:

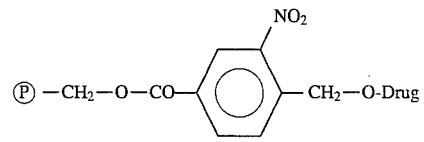

This compound can be photolysed to Drug-OH.

The choice of polymer may also be influenced by the body locality which is to be treated by the released drug. Different physical properties of the polymer may be required for proper diffusion at different body locations. For example, the ionic strengths of body fluids varies in different body locations and body organs, and this needs to be taken into account in selecting an appropriate polymer.

The polymer residue, after photo release of the drug therefrom, may be physically removed from the body, or left to be naturally dissolved or excreted over time. In one preferred embodiment, a biodegradable polymer, e.g. of polylactide copolymer is used, with a preselected rate of biodegradation to fit with the chosen rate of drug release therefrom. Then the question of residual polymer removal does not arise. Another method for arranging residual polymer removal is to choose a polymer which is sensitive to radiation of a wavelength different from that to which the photolabile group is sensitive, so that after drug release therefrom the polymer can be degraded to small, harmless, readily excreted products by radiation.

Coupling of the polymer to the photolabile linking compounds suitably takes place in solution, as does the subsequent coupling of the compound to the pharmaceutical. Water soluble compounds are preferred. However, it is preferable in some cases to administer the compound to the body as a water insoluble polymeric co-matrix or hydrogel, so as to be able to adjust the size of the particles of the material, to arrange for localization of it in the body organs where the treatment is needed. For this purpose, the polymer-drug compound of the present invention may be rendered insoluble by precipitation, and mixed with a water soluble polymer such as polyacrylic acid, in proportion appropriate to form a hydrogel, prior to administration.

The specific process of coupling BNBA, CPA or other carboxylic acid group containing compounds, to a hydroxyl-bearing polymer such as PVA, PEG, cyclodextrin or starch may involve initial conversion of the carboxylic acid group to an acyl chloride by a reaction with a thionyl chloride. Then the acyl halide is reacted with the polymer under standard conditions, to form ester linkages to the polymer, and yield a compound, in the case of BNBA, having pendant bromomethyl-nitro-benzoic acid groups of the following formula:

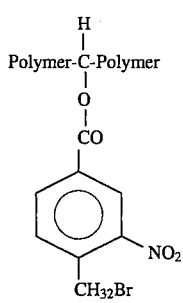

The pendant bromomethyl group is now available for reaction with a nucleophile on a therapeutic compound. Another polymer coupling method is the formation of mixed anhydrides of the acid group bearing linking compounds such as BNBA, and the subsequent reaction of the mixed anhydride with hydroxyl groups on the polymer. A third alternative is the reaction of the carboxylic acid groups on the compound with the hydroxyl groups on the polymer with the aid of a coupling reagent such as DCC, dicyclohexylcarbodiimide.

In a preferred embodiment of this system, the therapeutic compound contains a carboxylic acid group which links to the bromomethyl group with elimination of the bromine leaving group. To conduct this reaction, it is best initially to convert the free carboxylic acid group to a metal salt thereof, to increase its reactivity. The best salts for this purpose are the cesium and potassium salt, but others can be used if desired. The resultant product can be depicted as having a pendant chemical group from the polymer, thus:

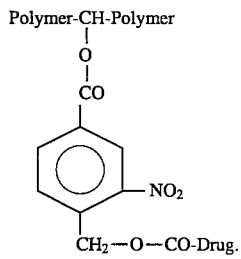

Upon appropriate radiation, the primary photochemical process is an intramolecular hydrogen abstraction by the excited nitro group. This is followed by an intramolecular rearrangement, with the —OH group moving to the carbon located at the ortho position on the ring. Electron redistribution results in formation of the unstable nitroso derivative, and this is followed by elimination of the carboxyl group. The overall chemical reaction can be represented thus:

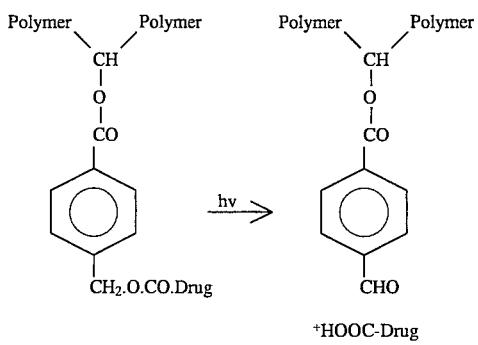

Thus, the original therapeutic compound formula has been restored, and it is released in therapeutically active form.

Other compounds analogous to BNBA can be used in the process of the present invention, for example, the chloromethyl and the iodomethyl analogs. However, these are less satisfactory than BNBA itself, since chlorine and iodine are less suitable as active groups than bromine, leading to greater difficulties in obtaining the necessary quantities of active therapeutic agent coupled to the complex. Nevertheless, provided the complex contains the nitro group located at a position on the benzene ring adjacent to the halomethyl group, appropriate lability of the grouping will be obtained.

Preparation of a polymer-drug compound with a carbamate linkage as discussed above may also be achieved by use of the aforementioned BNBA and a hydroxyl containing polymer. The polymer with pendant bromomethyl-nitrobenzoate groups can be hydrolyzed to a 4-hydroxymethyl compound, reacted with phosgene to prepare the oxycarbonyl chloride compound, and then reacted with the amino group of the drug to form the labile carbamate linkage thereto, as follows:

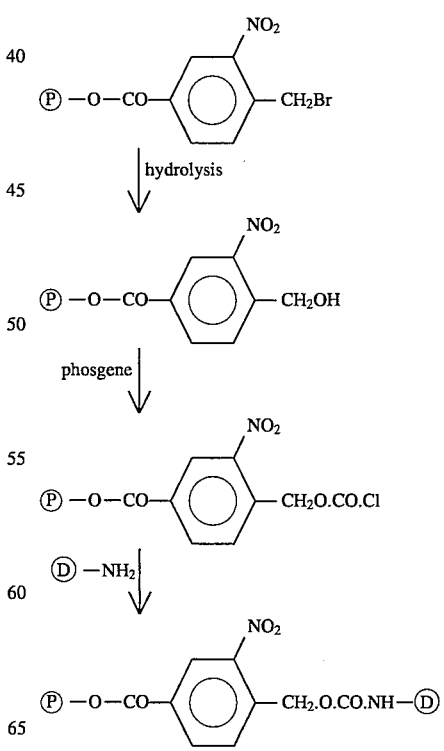

Whilst it is preferred to use compounds of this type such as BNBA which contain a benzene ring substituted only with nitro and halomethyl at the positions indicated, it is possible in the alternative to use compounds having benzene rings bearing other inert substituents at other positions on the ring, such as lower alkyl groups especially methyl. It is also halo-methyl group containing polymer, e.g. chloromethylated styrene, to a nitrovanilline derivative, followed by conversion of the 4-aldehydic group thereon to the oxycarbonylchloride, thus:

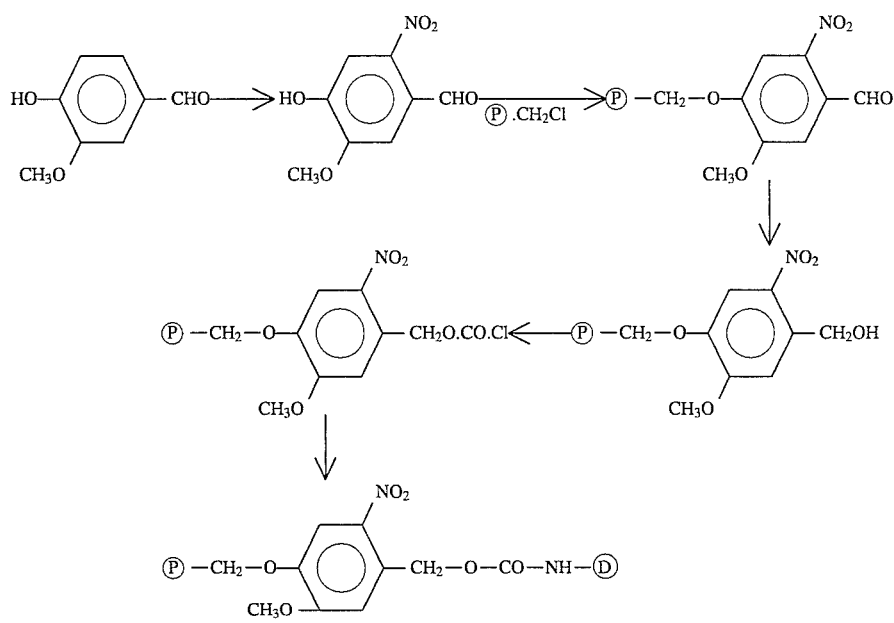

possible to use naphthalene analogs, provided that the necessary arrangement of halomethyl and nitro groups on the naphthalene nucleus analogous to BNBA is adopted.

The choice of CPA, [4-(2-chloropropionyl)phenyl]acetic acid, for providing the photolabile groups, as discussed above, in practice offers certain advantages over BNBA. In particular, the products formed after irradiation of the CPA-derived linkage are apparently more acceptable, being colourless and harmless, whereas those from BNBA are yellow, and may interfere with the further photolysis, i.e. by exhibiting a filter effect. The analogous compound obtained using CPA-type compounds and their photolysis can be represented as follows:

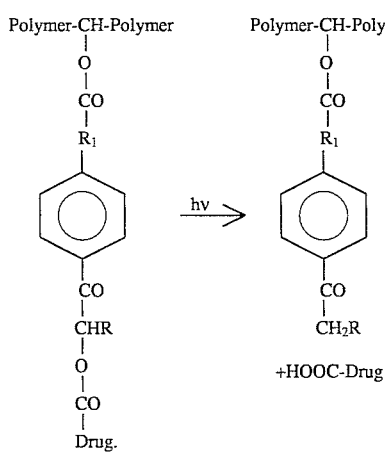

The aforementioned photolabile carbamate linkage to an amino-drug can alternatively be created by coupling a Similarly when the drug is linked via an amino group thereon, through a carbamide linkage as previously described, the analogous compound and its photolysis can be represented thus:

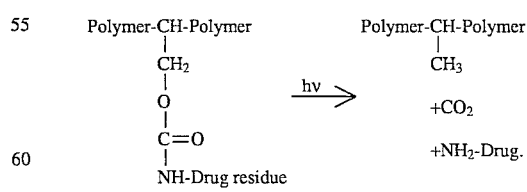

When the attachment of the drug to the polymer is by use of a hydroxyl or phenol group on the drug, the attachment and release reactions using Polymer-BNBA compounds and polymer-CPA compounds can be exemplified as follows:

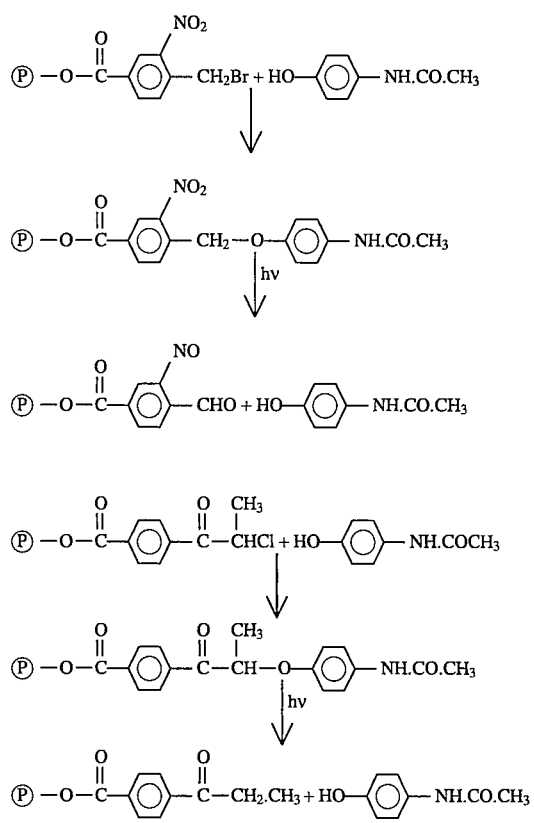

When the attachment of the drug to the polymer is by use of a carboxyl group on the drug, the coupling reaction can be by use of a 4-hydroxymethyl, 3-nitrobenzoic acid derivatized polymer, thus:

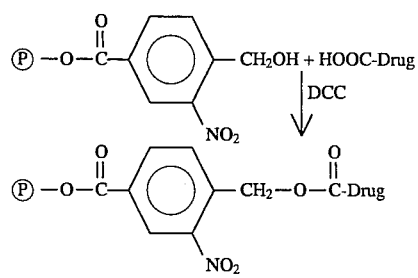

A very wide range of therapeutic agents can be incorporated in complexes according to the present invention, for controlled release at the required locations in the body. It is merely required that the chemical structure of the therapeutic compound contain a nucleophile group such as carboxylic acid, amino or hydroxyl, which will attach to the light sensitive linkage of the polymer compound. Examples of such therapeutic compounds include acetylsalicylic acid (aspirin), indomethacin, nicotinic acid, naproxen, ibuprofen, cimetidine, ranitidine, cycloserine, flucytosine, amantadine, benzocaine, penicillin V, acetaminophen, cortisone, etc. Anti-inflammatory drugs are particularly useful in the present invention. Administration of a complex with an anti-inflammatory drug, by direct injection into the vicinity of an inflamed joint of a patient, is one of the specific, preferred applications of the products and processes of the present invention.

Most advantageously, however, the complexes of the present invention utilize cancer-treating drugs, for which the specificity and location of action requirements are the most severe. Such drugs include methotrexate (which has both carboxylic acid and amino nucleophilic groups in its structure), 5-fluorouracil (which has suitable secondary amino groups in its structure), chlorambucil (which has a carboxylic acid group in its structure), melphalan (which has both carboxylic acid and amino groups in its structure), cytarabine (which has amino groups in its structure), cyclophosphamide (which has secondary amino groups in its structure), busulfan, dactinomycin and mithramycin. A specific advantageous application of the products and processes of the present invention is the injection thereof to sites in a patient's body from which a malignant tumor has recently been removed. The site may still contain some malignant cells, which can then be treated according to the present invention.

The second general embodiment of the invention involves the use of insoluble polymeric complexes of biologically acceptable polymers in which the drug is physically dispersed, and which are capable of swelling in water. On suitable radiation, they undergo a dimensional change, and release the drug from dispersion therein in a controlled manner, so that the rate of release is controlled by the dosage of radiation. Suitable photolabile groups for use in this system are those derived from malachite green, and in monomeric form corresponding to the formula:

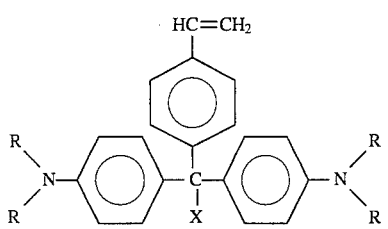

in which each R group is the same or different and is selected from lower alkyl, e.g. methyl or ethyl, and X is hydroxy or nitrile. They can be prepared from 4-bromostyrene via Grignard methods using Michler's ketone, the reaction being conducted at relatively low temperatures to avoid spontaneous polymerization. The products where X is hydroxyl (leuco carbinols) can be converted to the corresponding nitriles by reaction with potassium cyanide. The nitriles are more stable than the carbonyls, especially under acidic conditions.

Such monomeric compounds when incorporated in polymers such as polyacrylamide, poly(N-isoporopylacrylamide), HEMA, dihydroxypropyl methacrylate, copolymers and mixtures thereof, and the like, in crosslinked, complex (hydrogel) form, cause the polymer to swell on photoirradiation. Upon exposure to light of wavelength greater than 200 nm, the compounds undergo ionization to produce leuco carbonation. The electrostatic forces produced are capable of expanding the polymer complex on the order of 1000%, to release a drug dispersed therein. The leuco carbonation reverts back to the non-ionized form in the dark, so that the system is reversible. At the termination of the radiation, the polymer complex retracts to hold the residual drug in the matrix. In this way, control is exercised over the amount of drug released.

In a specific example of this second general embodiment of the invention, a copolymer of p-NIPAM (poly-(N-isopropylacryl-amide)) and the triphenylmethylene leucohydroxide derivative (1 mole percent) results in a material which, upon radiation, will exhibit a lower critical solution temperature (cloud point or precipitation temperature) of 37° C., which is 5° C. above the normal level for p-NIPAM in water. This effect will enhance control of the release rate of the drug upon exposure to radiation. Thus at normal body temperatures, the polymer remains in solution and any drug dispersed therein is tightly held and not released. Upon appropriate incident radiation, the triphenyl compound acts a photosensitizer, creates electrostatic forces and expands the gel so that the drug is released. When the radiation is cut off, the gel contracts again to stop release of the drug.

A wide range of other polymers exhibit similar photochemical effects, and can be used in this embodiment of the present invention. Upon irradiation, they convert photochemically from a hydrophobic form to a hydrophilic form, either reversibly or irreversibly, to release a drug physically dispersed therein. Specific examples are polymer incorporating a t-butyl ketone group in a side chain immediately adjacent to the polymer backbone, i.e polymers derived from copolymerization of a monomer mixture which includes t-butyl vinyl ketone. The polymer causing pendant t-butyl ketone groups is hydrophobic, but is photochemically converted to aldehyde on suitable irradiation, to become hydrophilic. This is an example of an irreversible photochemical change.

Suitable crosslinkers for use in forming the above complexes include methylene bisacrylamide, triethyleneglycol dimethacrylate and tetraethyleneglycol dimethacrylate.

Another specific embodiment of the invention which combines features of the first and second general embodiments discussed above is a drug covalently coupled to a polymer through the intermediary of a photolabile bond, and then incorporated in a hydrogel or similar matrix by complexing it with a water compatible polymer, e.g. polyacrylic acid. Such a combination is a soft solid, with a degree of shape retention, and is suitable for implantation as a body into a treatment site. Such an embodiment is well adapted for the preferred treatments, namely local inflammation of joints and tumor-removal sites discussed above.

The third general embodiment of the invention involves, in one aspect, active therapeutic agents encapsulated in photochemically degradable polymeric films. Such photodegradable films are known. They are commonly based upon copolymers of ethylenically unsaturated monomers such as ethylene, styrene, methylacrylate, methylmethacrylate and the like, with unsaturated ketones in minor amount, for example methylvinyl ketone, methylisopropenyl ketone, phenyl vinyl ketone and phenyl isopropenyl ketone. Upon exposure to ultraviolet light, the ketone groups initiate a photodegradation of the polymer, thereby releasing drug encapsulated therein. Polymers used for such encapsulation embodiments in the present invention should ideally be water soluble for encapsulation but become water insoluble during encapsulation. They should ideally also be water soluble after degradation, and both biodegradable and biocompatible. Preferred such polymers for use in the present invention are derived from hydroxyethyl methacrylate (HEMA), methacrylic acid and methylmethacrylate with the ketone monomers in minor amounts.

The invention is further described in the following specific examples. In the examples, in some cases, there are reported the preparation and testing of model compounds, the behaviour of which on photolysis is indicative of their behaviour to be obtained on the analogous compounds of the invention. Thus, when the photolabile group-containing linking compound 3-nitro-4-bromomethylbenzoic acid (BNBA) is coupled to a drug, and residual, acid group is esterified with a lower alkyl group, e.g. ethyl, instead of coupled to a polymer via the same ester linkage, the behaviour on radiation of the lower alkyl ester analogue is reliably predictive of the behaviour of the corresponding polymeric ester, the same chemical groupings being involved.

SPECIFIC DESCRIPTION THE MOST PREFERRED EMBODIMENTS

The invention will be further described with reference to the following specific examples, for illustrative purposes only.

EXAMPLE 1

3-nitro-4-bromomethylbenzoic acid (BNBA) was prepared by the method described in the paper by D. H. Rich and S. K. Gurwara, *J. Amer. Chem. Soc,* 97, 1575 (1975).

BNBA was coupled to polyethyleneglycol PEG-300 as follows:

BNBA (230 mg, 1 mMol) was refluxed for one hour with thionyl chloride (1 ml). The reaction mixture was evaporated to dryness, and PEG (MW 300; 150 mg, 0.5 mMol) in dry toluene (4 ml) was added. It was refluxed for four hours under a slow stream of nitrogen. The reaction mixture was extracted with ethyl acetate (50 ml, twice) and the organic layer was washed with 5% NaOH (30 ml, twice) and water (50 ml, twice). It was dried over magnesium sulphate, filtered and evaporated. The resulting product was analyzed by UV, NMR and IR spectroscopy, which confirmed the identity of the desired product.

EXAMPLE 2

The BNBA-PEG (300) coupled product prepared according to Example 1 was reacted with indomethacin to form a drug-photolabile group-polymer compound according to the invention, as follows:

Indomethacin cesium salt was prepared by treating indomethacin (36 mg, 0.1 mMol) in methanol (5 ml) with cesium bicarbonate $CsHCO_3$ (20 mg, 0.1 mMol) dissolved in water (1 ml). The solvent was evaporated and the salt was dried over phosphorus pentoxide in high vacuum (1–2 mmHg). The dry salt was treated with BNBA-PEG (300) (25 mg, 0.05 mMol) dissolved in dried DMF (2 ml).

The reaction mixture was extracted with ethyl acetate (30 ml, twice) and the organic layer was washed with 5% NaOH (25 ml, twice) and water (25 ml, twice). It was dried over magnesium sulphate, filtered and evaporated. Yield: 50% The resulting product was analyzed by UV and NMR spectroscopy, which confirmed its identity.

EXAMPLE 3

Ethyl (3-nitro-4-methyl indomethacinate)benzoate (INBA-Et) was prepared by the following procedure.

The cesium salt of indomethacin was prepared by treating indomethacin (1 mMol) in methanol (5 ml) with cesium bicarbonate $CsHCO_3$ (200 mg, 1 mMol) dissolved in water (1 ml). The solvent was evaporated and the salt was dried over phosphorous pentoxide in high vacuum (1–2mmHg). The dry salt was treated with the ethyl ester of BNBA (70 mg, 0.27 mMol) dissolved in dry dimethylformamide (2 ml). It was stirred overnight at room temperature. The reaction mixture was extracted with ethylacetate (30 ml, twice) and the organic layer was washed with 5% sodium hydroxide (25 ml, twice) and water (25 ml, twice). It was dried over magnesium sulfate, filtered and evaporated. A yield of 80% was obtained. UV and NMR spectra were taken to confirm the product. Further checking of identity and purity of the product was conducted by thin layer chromatography and high performance liquid chromatography.

EXAMPLE 4

The product produced according to Example 3 was subjected to photolysis. In this and in all other photolysis experiments reported herein, irradiation was performed in an RPR-100 apparatus (Rayonet, the southern company, Middleton, Conn.) equipped with 3000-A lamps. The drug derivatives were irradiated in absolute ethanol at concentrations 0.03 to 0.003 molar in pyrex tubes. Dissolved air was removed from the solution by passing nitrogen through it for ten minutes. Irradiation time was up to 240 minutes, and samples were taken during irradiation and analyzed by HPLC and by TLC. For HPLC analysis, an ODS, LC-18, 150 mm, 4.6 mm column was used. Eluents were methanol or methanol:buffer mixtures. The buffer was 0.1 molar $NaH_2PO_4$. The flow rate was 1 ml per minute.

The photolysis of the product of Example 3 was conducted in concentration 0.003 molar. HPLC analysis was conducted, using the aforementioned buffered eluent. A decrease in the percentage of INBA-ET in proportion to irradiation time up to 60 minutes was observed, the amount of INBA-ET in the mixture after 6 minutes of irradiation being 2%. Indomethacin was detected in all samples which had been subjected to irradiation.

EXAMPLE 5

Ethyl (3-nitro-4-methylnicotinate)benzoate, (NNBA-Et), was synthesized by the method described in Example 3, starting from the molar equivalent of nicotinic acid cesium salt. An 80% yield was obtained. The product was pure after extraction, and its structure and purity were confirmed by UV and H-NMR spectroscopy.

EXAMPLE 6

NNBA-Et produced according to Example 5 above was subjected to photolysis, under the conditions described in Example 4. The photolysis was carried out in two different concentrations, 0.03 molar and 0.003 molar. In the more dilute solution, photolysis was complete in three hours, whilst in the more concentrated solution, only 30% of the starting compound was photolyzed. The HPLC analysis was conducted using the buffered methanol. FIG. 1 of the accompanying drawings is a graphical presentation of the results of the irradiation of the more dilute solution, with % product plotted as vertical axis and minutes of irradiation plotted as horizontal axis. The circular plots indicate the amount of NNBA-Et, and the solid plots indicate the amount of free nicotinic acid.

EXAMPLE 7

Nicotinic acid (NA) cesium salt was prepared as described in Example 5. The NA-Cs salt so formed was coupled to a BNBA-PEG (8,000) compound prepared by refluxing BNBA (230 mg, 1 mMol) for one hour with thionyl chloride (1 ml), evaporating to dryness, adding thereto PEG (MW 8000; 4 g, 0–5 mMol) in dry toluene (10 ml), refluxing for 16 hours under a slow stream of nitrogen, precipitating the polymer by adding the cooled reaction mixture dropwise to a stirred ether solution (800 ml), filtering, washing and reprecipitating from ether. Thus, NA-Cs salt (0.5 gm, 2 mMol) in DMF (2 ml) was added to BNBA-PEG (4 gm, 0.5mMol) dissolved in DMF (6 ml). The reaction time was 24 hours. Then the reaction mixture was added slowly to a stirred ether solution (1 liter) and the polymeric product precipitated and was recovered and purified by recrystallization from ethanol:ether. A yield of 3 gm (75%) was obtained, after 3 recrystallizations.

EXAMPLE 8

The NNBA-PEG drug-polymer coupled product produced according to example 7 was subjected to photolysis as previously described. An 18 mg (0.0023 mMol) sample in absolute ethanol (1 ml) was irradiated for 2 hours. The irradiated sample was filtered through a small silica gel column, and eluted with ethanol (10 ml). According to TLC, only nicotinic acid was present in the filtrate. Its amount, calculated on the UV absorption of the filtrate, was 0.002 mMol.

EXAMPLE 9

The BNBA-PEG(300) coupled product described in Example 1 was coupled to nicotinic acid through a photolabile bond as follows:

BNBA-PEG (300) (0.25 mMol), nicotinic acid NA (123 mg, 1 mMol), dry potassium fluoride (KF 116 mg, 2 mMol) in dry DMF were stirred at 50° C. for 24 hours. The reaction mixture was extracted with ethylacetate (30 ml, twice) and the organic layer washed twice with 5% NaOH (25 ml) and water (25 ml). It was dried over magnesium sulfate, filtered and evaporated. A yield of 30% was obtained. UV and H-NMR spectra confirmed the identity of the product.

The product so obtained (18 mg, 0.02 mMol) was subjected to photolysis in solution (0.01 Molar) in absolute ethanol (2 ml) for two hours. Using TLC analysis, the presence of nicotinic acid was detected.

EXAMPLE 10

A BNBA-poly(hydroxyethyl methacrylate) compound, BNBA-PHEMA, was prepared by polymerizing HEMA (1.3 gm, 10 mMol), in dry DMF (6 ml) in the presence of 25 mg of AIBN, at 60° C. for 2 hours and at 80° C. for 2 hours under a nitrogen current. After the polymerization was completed, the reaction mixture was cooled to room temperature and a few grains of hydroquinone monomethylether and pyridine (1 gm) were added. Then a solution of BNBA-Cl (3 gm, 12 mMol) in DMF (4 ml) was added. The reaction mixture was stirred at 50° C. overnight and poured over methanol (200 ml), and the polymer precipitated. It was reprecipitated twice from DMF:ether. TLC indicated that no BNBA was present.

Nicotinic acid was then reacted with the BNBA-PHEMA so formed, by stirring in a solution in dry DMF (16 ml) BNBA-PHEMA (400 mg, 1 mMol), nicotinic acid (625 mg, 5 mMol), dry potassium fluoride (600 mg, 10 mMol) and stirring at 50° C. for 24 hours. The cooled reaction mixture was added dropwise to a stirred ether solution (300 ml). The polymer precipitated. It was filtered and washed with ether and with methanol. The product was dissolved in DMF. TLC indicated no traces of free NA.

EXAMPLE 11

The NMBA-PHEMA prepared according to Example 10 was subjected to photolysis as described above, for two hours. Nicotinic acid was present in the resulting solution, according to TLC.

EXAMPLE 12

Ethyl [4-(2-propionyl nicotinate)phenyl]acetate, NPA-ET.

CPA (230 mg, 1 mMol) in thionyl chloride (1 ml) was refluxed for one hour. The reaction mixture was evaporated to dryness, absolute ethanol (3 ml) was added, and the solution was refluxed for two hours. The ethanol was evaporated to give pure ethyl-CPA, according to TLC, in a yield of 98%.

NPA-ET was prepared from ethyl CPA by two different routes.

A. Nicotinic acid-cesium salt was prepared by treating nicotinic acid (123 mg, 1 mMol) in methanol (5 ml) with cesium bicarbonate (300 mg, 1 mMol) dissolved in water (1 ml). The solvent was evaporated and the salt was dried over phosphorus pentoxide in high vacuum (1–2 mmHg). The dry salt was treated with CPA-ET as prepared above—(70 mg, 0.27 mMol) dissolved in dry DMF (2 ml). It was stirred overnight at room temperature. The reaction can be completed in four hours by heating it to 50° C. The reaction mixture was extracted with ethylacetate (30 ml, twice) and the organic layer was washed with 5% NaOH (25 ml, twice) and water (25 ml, twice). It was dried over magnesium sulfate, filtered and evaporated. The yield was 75%.

B. CPA-ET (70 mg, 0.27 mMol), nicotinic acid (125 mg, 1 mMol), dry KF (116 mg, 2 mMol) in dry DMF (3 ml) were stirred at 50° C. for 24 hours. The reaction mixture was extracted with ethylacetate (30 ml, twice) and the organic layer was washed with 5% sodium hydroxide (25 ml, twice) and water (25 ml, twice). It was dried over magnesium sulfate, filtered and evaporated. A 70% yield was obtained.

TLC analysis and UV and H-NMR spectroscopy confirmed the identity of the products.

The NPA-ET compound so prepared was subjected to photolysis in absolute ethanol (10 mg in 1 ml), by irradiation for 75 minutes, samples being taken every 15 minutes, diluted tenfold and analyzed by HPLC using as eluent a 10% buffer in methanol. A gradually increasing percentage of nicotinic acid was detected in the samples, in accordance with the time of irradiation, until, after 75 minutes, the mixture contained 93% nicotinic acid, and only 6% of residual NPA-ET.

EXAMPLE 13

NPA-PEG (8000)

CPA (115 mg, 0.5 mMol) was refluxed for one hour with thionyl chloride (1 ml). The reaction mixture was evaporated to dryness and PEG (molecular weight 8000; 1 gr, 0.125 mMol) in dry toluene (5 ml) was added. It was refluxed for 16 hours under a slow stream of nitrogen. The cooled reaction mixture was added dropwise to a stirred ether solution (200 ml). The polymer precipitated, it was filtered and washed three times with ether. The product was dissolved in ethanol (5 ml) and precipitated again by adding it dropwise to a stirred solution of ether (200 ml). Yield—0.95 gm (95%). TLC analysis revealed no traces of freed CPA.

The CPA-PEG as prepared above was then coupled to nicotinic acid. CPA-PEG (160 mg, 0.02 mMol), NA (25 mg, 0.2 mMol), dry KF (25 mg, 0.04 mMol) in dried DMF (2 ml) were stirred at 50° C. for 24 hours. The cooled reaction mixture was added dropwise to a stirred ether solution (150 ml). The polymer precipitated, it was filtered and washed twice with ether. The product was dissolved in ethanol (5 ml) and precipitated again by adding it dropwise to a stirred volume of ether (150 ml). TLC analysis revealed no traces of free NA.

The NPA-PEG compound so formed was subjected to photolysis by irradiating a 20 mg solution thereof in absolute ethanol for two hours, the concentration being 0.0025 Molar. TLC analysis revealed the presence of nicotinic acid in the solution.

EXAMPLE 14

4-Acetamidophenol (paracetamol, PAM) was coupled to a polymer-mimicking group using CPA, namely CPA-ET previously described, via a hydroxyl group on the drug, and photolysed to demonstrate release of the drug therefrom.

The reaction scheme can be depicted as follows:

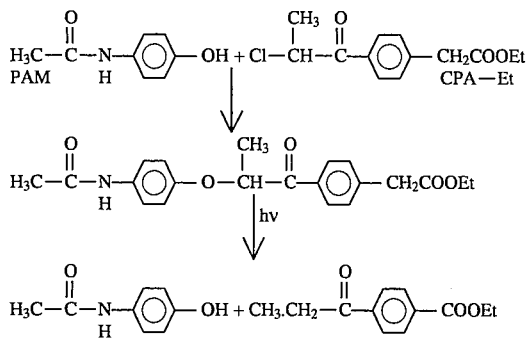

PAM (32 mg, 0.02 mM) in dry DMF (2 ml) was treated with sodium methoxide (10 mg, 0.2 mM). After one hour, CPA-ET (26 mg, 0.1 mM) in DMF (1 ml) was added. After a reaction time of 48 hours, the reaction mixture was extracted with ethylacetate and water and the organic layer was washed twice with 5% NaOH and water. It was dried over magnesium sulfate, filtered and the solvent was evaporated to dryness. A 40% yield (16 mg) was obtained. The identity of the product was confirmed by UV and NMR spectroscopy, and TLC analysis.

The compound so formed was subjected to photolysis, as a 0.001 Molar solution in ethanol (4 mg in 10 ml). It was irradiated for 20 minutes, and the irradiated solution was analyzed on HPLC and TLC. In both analyses, it was clearly observed that pure PAM was present in high yield, whilst no coupled compound was detected.

EXAMPLE 15

SYNTHESIS OF N-ISOPROPYLACRYLAMIDE (NIPAM) HYDROGEL

The NIPAM hydrogel containing a small amount of triphenylmethane leucohydroxide (TPMLH, $R=N(CH_3)_2$) was prepared by free radical polymerization as follows:

N-isopropylacrylamide (1.94 g), N,N'-methylenebisacrylamide (0.60 mg), diphenyl-4-vinylphenylmethane leucohydroxide (0.04 g) and 2.2'-azoisobutyronitrile (0.05 g) were dissolved in 2 ml of dimethyl sulfoxide (DMSO), the solution degassed and heated at 60° C. for 24 hours. The gel was immersed in DMSO overnight and then in water to extract unreacted monomer.

Photo release studies were conducted on the hydrogel so formed. The NIPAM hydrogel was cut into small pieces occupying a volume of 2–4 ml and was then placed in a methylene blue (MB, $1.20\times10^{-5}$M or 5 ppm) solution for a period of 48 hours. After equilibration the gel was removed from the MB solution, washed with distilled water and placed in a UV cuvette containing 3.0 ml of distilled water. Photo-activated release of the dye trapped within the NIPAM gel was demonstrated by monitoring the increase in the absorbance maximum of MB in the outer water phase at 654 nm. UV spectra were recorded every 4 minutes over a period of 20 minutes for one sample in the dark (sample compartment of the HP spectrophotometer) and the other irradiated in a Rayonet photochemical reactor. The photo-activated release profile of NIPAM gel over a 20 minute period is shown in FIG. 2; (1) in the dark (2) irradiated with light of 300 nm.

EXAMPLE 16

A drug covalently coupled to a polymer through the intermediary of a photolabile bond was incorporated in a hydrogel to form a shape-retaining, implantable body.

A polymer-drug compound PEG 6000-BNBA-nicotinic acid was prepared by processes generally as previously described. The polymer (16.5 g) was dissolved in distilled water (15 g), and the solution added gradually over 5 seconds under high speed stirring conditions to a 2% aqueous solution of polyacrylic acid (75 g, 1.5 g PAA). Stirring was continued for 15 minutes. A yellowish clear paste was obtained.

10% aqueous sodium chloride solution (25 g) was added, under less vigorous stirring conditions, gradually over 50 seconds. Precipitation of lumps of material occurred, and over 10 minutes stirring the lumps consolidated to form a yellowish sticky gum. After settling for 15 minutes, the aqueous liquor was poured off, the gum was consolidated with a spatula to squeeze out more liquid, distilled water (20 ml) added to rinse out NaCl and the mixture was swirled. After further soaking and squeezing, more water was poured off, and 4.5 g of rubbery yellowish gum solid, of solid content 29.37%, was obtained—a 44% yield.

0.4600 of this hydrogel was spread onto a piece of filter paper ($3.5\times2$ cm$^2$) and left to dry on a glass plate in a cabinet overnight at relative humidity 30%. The uncoated filter paper edges were pressed with plastic blocks to ensure non-wrinkling of the paper on drying. A yellowish coating formed on the filter paper. This indicated that the hydrogel lost 72% water on air-drying at room temperature. The coated filter paper was kept in an amber coloured sample bottle. This filter paper had 0.1288 g dry coating of the complex polyacrylic acid-PEG-6000-BNBA-nicotinic acid or 0.002 g nicotinic acid.

The remaining gum, 3.747 g, was treated with increasing amounts of distilled water until all dissolved and formed a non-flowing aqueous gel which had a slightly pink colour and weighed 10 g. This gum was estimated to contain 0.165% nicotinic acid (w/w).

500 mg of the hydrogel prepared as described above, with an attached nicotinic acid content of 0.016%, was suspended in methanol (5 ml) and air was removed with a stream of nitrogen. It was irradiated for 4 hours in the usual conditions.

The solvent was evaporated, methanol (25 ml) was added and shaken strongly. The methanol solution was taken out and evaporated to leave 0.5 ml solution.

TLC (AcOH:nBuOH:EtOHc) (1:1:1:1) shows clearly the presence of free pure nicotinic acid in the solution.

EXAMPLE 17

A drug containing a primary amino group, namely the anti-viral drug adamantamine, of formula:

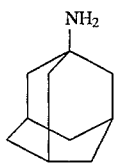

was coupled to a polymer via a photolabile chemical linkage utilizing the amino group of the drug, and then released in unchanged form by photolysis.

Adamantamine (10 mg, 0.06 mM) in dry dimethylformamide (1 ml) was treated with 4-oxycarbonylchloromethyl-3-nitrobenzoic acid ethyl ester (ONBA-Et, 10 mg, 0.025 mM) in dry dimethylformamide. It was stirred at room temperature for one hour. The reaction mixture was extracted with ethyl acetate (40 ml) and water (20 ml) and the organic layer was washed with 5% HCl (25 ml, three times), 5% NaOH (25 ml, three times), and water (25 ml, twice). It was dried over magnesium sulfate, filtered and evaporated. A yield of 8 mg (80%) ethyl (3-nitro-4-methyl-adamantcarbamate) benzoate, ADANABA-Et, was obtained, and its identity checked by TLC, UV spectroscopy and NMR spectroscopy.

ADANBA-Et so obtained (1.2 mg, 0.003 mMol) in absolute ethanol (1 ml) was irradiated for ten minutes, a sample being taken after five minutes. By TLC, in eluent A, adamantamine was detected, Rf 0.5. The spot of adamantamine of the TLC plate was coloured with ninhydrin solution. Its concentration was much higher after the longer irradiation time. The ADANBA-Et was analyzed with eluent E. Its concentration decreased upon irradiation and only traces of it were present after ten minutes of irradiation.

We claim:

1. A macromolecular complex of a therapeutically effective amount of a therapeutic substance and a biologically acceptable polymer, covalently chemically bonded thereto through the intermediary of a photolabile covalent chemical bond, said complex being effectively therapeutically inert and biologically acceptable for administration to a mammal, the complex being capable upon incidence of radiation of appropriately chosen characteristics to release the therapeutic substance therefrom in a therapeutically active form.

2. The complex of claim 1 wherein the photolabile covalent chemical bond derives from a photolabile peptide blocker compound.

3. The complex of claim 1 wherein the photolabile covalent chemical bond is a chemical grouping of an oxymethylene bond with the oxygen thereof covalently bound through its second valence link to the therapeutic substance group, and the methylene group bound through its second valence link to an aromatic nucleus at a position adjacent to a nitro substituent.

4. The complex of claim 3 wherein the aromatic nucleus of the grouping is benzene.

5. The complex of claim 4 wherein benzene nucleus is unsubstituted otherwise than by said nitro substituent, and is convalently chemically linked to said polymer at the position para to that of the methylene group.

6. The complex of claim 1 wherein the photolabile covalent chemical bond is derived from reaction of 3-nitro-4-bromomethylbenzoic acid coupled to the polymer at its position para to the bromo-methyl group, with a nucleophilic group on the therapeutic substance.

7. The complex of claim 1 wherein the photolabile chemical bond is derived from reaction of a compound of general formula:

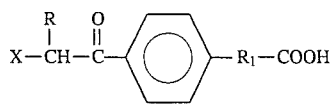

in which X is halogen, R is H or C1–C4 lower alkyl and R1 is C1–C4 alkylene, with a polymer through its carboxyl group and with the drug through its halo group.

8. The complex of claim 1 wherein said compound is [4-(2-chloropropionyl)phenyl]acetic acid.

9. The complex of claim 6 wherein the nucleophilic group on the therapeutic substance is a carboxylic acid group.

10. The complex of claim 1 wherein the polymer has a plurality of hydroxyl groups per molecule.

11. The complex of claim 10 wherein the polymer is selected from the group consisting of starch, starch derivatives, cyclodextrin, polyvinyl alcohol, polyethylene glycol and poly(hydroxyethylmethacrylate) and copolymers thereof.

12. The complex of claim 11 wherein the therapeutic substance is an anti-inflammatory agent.

13. The complex of claim 11 wherein the therapeutic substance is an anti-tumor agent.

14. The complex of claim 1 wherein the photolabile covalent chemical bond is a carbamate linkage from an amino group of the therapeutically active substance.

15. The complex of claim 14 including a nitrobenzene group interposed between the polymer and the carbamate linkage.

16. The complex of claim 1 wherein the photolabile covalent chemical bond is a keto aromatic group.

17. The complex of claim 16 wherein the keto aromatic group is linked to the therapeutic substance through an ether linkage, which on photolysis reforms a hydroxyl group on the therapeutically active substance.

18. A macromolelcular complex of a therapeutically effective amount of a therapeutic substance and a biologically acceptable polymer, the therapeutic substance and a biologically acceptable polymer, the therapeutic substance being diffused into a hydrogel of the biologically acceptable polymer, the hydrogel being susceptible to dimensional change upon exposure to light of appropriate wavelength, to release the therapeutic substance therefrom during such exposure.

19. The complex of claim 18 wherein the dimensional change is reversible.

20. The complex of claim 19 wherein the polymer of the hydrogel has attached thereto malachite green derivative groups.

21. The complex of claim 20 wherein the polymer of the hydrogel is derived form polymerization of acrylamide, 2-hydroxyethyl methacrylamide, dihydroxypropyl methacrylate, methylene bisacrylamide, tetraethyleneglycol dimethacrylate or triethyleneglycol dimethacrylate.

22. The complex of claim 1 wherein the therapeutic substance is enclosed in a capsule of photodegradable polymeric material.

23. The complex of claim 22 wherein the photodegradable polymeric material is a copolymer containing polymerized groups derived from methyl vinyl ketone or methyl isopropenyl ketone, phenyl vinyl ketone or phenyl isopropenyl ketone.

24. The complex of claim 23 wherein the photodegradable polymeric material is a copolymer of methacrylic acid or methyl methacrylate with one of methylvinyl ketone and methylisopropenyl ketone, phenyl vinyl ketone and phenyl isopropenyl ketone.

* * * * *